United States Patent [19]

Scheunemann et al.

[11] Patent Number: 4,590,267
[45] Date of Patent: May 20, 1986

[54] CRYSTALLINE DISODIUM SALT OF CEFODIZIM

[75] Inventors: Karl-Heinz Scheunemann, Frankfurt am Main; Burkhard Mencke, Holzappel; Jürgen Blumbach, Frankfurt am Main; Walter Dürckheimer, Hattersheim am Main; Klaus Fleischmann, Eschborn, all of Fed. Rep. of Germany

[73] Assignee: Hoechst Aktiengesellschaft, Frankfurt, Fed. Rep. of Germany

[21] Appl. No.: 770,406

[22] Filed: Aug. 28, 1985

Related U.S. Application Data

[63] Continuation-in-part of Ser. No. 430,765, Sep. 30, 1982, abandoned.

[30] Foreign Application Priority Data

Nov. 3, 1981 [DE] Fed. Rep. of Germany ....... 3143537

[51] Int. Cl.$^4$ ........................................... C07D 501/56
[52] U.S. Cl. ...................................................... 544/27
[58] Field of Search ........................... 544/27; 514/206

[56] References Cited

U.S. PATENT DOCUMENTS 4,278,793  7/1981  Durckheimer et al. ............. 544/27

OTHER PUBLICATIONS

R. Wise et al, The Lancet, (Sep. 10, 1983) pp. 624–625.

Primary Examiner—Donald G. Daus
Assistant Examiner—Mary E. Ceperley
Attorney, Agent, or Firm—Curtis, Morris & Safford

[57] ABSTRACT

A crystalline water soluble disodium salt of 7-β-[2-(2-aminothiazol-4-yl)-2-syn-methoximinoacetamido]-3-(5-carboxymethyl-4-methyl-1,3-thiazol-2-ylthiomethyl)-ceph-3-em-4-carboxylic acid (cefodizim), or an adduct or solvate thereof with water and/or an organic solvent.

1 Claim, No Drawings

CRYSTALLINE DISODIUM SALT OF CEFODIZIM

This application is a continuation-in-part of application Ser. No. 430,765 filed Sept. 30, 1982, now abandoned.

The invention relates to crystalline water-soluble salts of 7-β-[2-(2-aminothiazol-4-yl)-2-syn-methoximinoacetamido]-3-(5-carboxymethyl-4-methyl-1,3-thiazol-2-ylthiomethyl)ceph-3-em-4-carboxylic acid of the formula I,

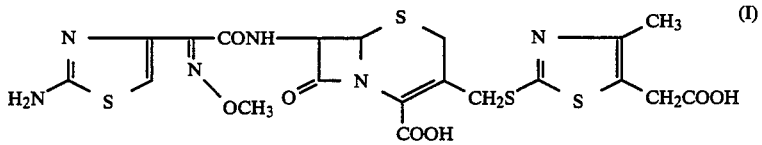

which also has the generic name of cefodizim, and to a process for their preparation.

Cefodizim (cf. Belgian Pat. No. 865,632) has, in addition to a high antibacterial activity and pronounced β-lactamase stability, a markedly prolonged half-life of elimination. These properties make it a valuable antibiotic. Cefodizim cannot be used parenterally because of its extremely low water solubility. In contrast, its amorphous and crystalline water soluble salts are particularly suitable for parenteral use. The crystalline water soluble salts of cefodizim are not described in Belgian Pat. No. 865,632.

For a number of reasons, it is worth attempting to obtain the salts of cefodizim in a crystalline form. Thus, in general, a high purity of the product is obtained by crystallization. More in particular, the crystalline salts of the invention, particularly the disodium salt, are relatively free of thiol side chain impurities present in the free acid precursor from which they are prepared, said impurities stemming from the synthesis of the parent acid and present in the reaction mixtures from which the free acid compound is recovered.

In addition, in those cases where solvents, or other materials used in the preparation of the salt, are intercalated or absorbed in the crystal lattice, it is possible in this manner to obtain products of defined or reproducible composition. By this means, the product can be easily standardized. Furthermore, crystalline materials are more easily manipulated than amorphous materials. This is of great importance, especially during the isolation of the product, for example by filtration or centrifugation. However, the ease of filling is also enhanced, for example by the increased flowability.

Thus the invention had the object of preparing crystalline water soluble salts of cefodizim of the formula I, as well as its adducts or solvates with water or organic solvents.

The processes described in the patent and other literature for the preparation of crystalline salts of a very wide variety of cephalosporins, when applied to cefodizim, did not lead to the desired result. Thus, the process described in German Offenlegungsschrift No. 2,709,439 for the preparation of a crystalline sodium salt of cefotaxim could not be employed with success. In this process, crystallization of the salt from methanolic solution occurs at room temperature. The solubility of the disodium salt of cefodizim is, however, compared to the sodium salts of other cephalosporins, extremely high.

Likewise, the specific freeze-drying process described in German Offenlegungsschrift No. 2,614,668 for the preparation of crystalline sodium salts of, for example, cefaloridine, cefolotin or cefazolin, only led to an amorphous disodium salt of cefodizim.

Considering this state of the art, it could not be expected that attempts to convert cefodizim into excellently crystalline salts would have success.

It has now been found that crystalline water soluble salts of cefodizim are obtained when the acid of the formula I is brought into solution in water with at least twice the equivalent amount of a basic compound. If necessary, an organic solvent which is miscible with water is added to this solution until crystallization occurs and, if desired, the organic solvent and, optionally, also the water are removed from the adducts and solvates thus obtained.

The basic compound can be employed in a slight excess, but preferably in an amount of 2 moles relative to one mole of cefodizim.

Inorganic and organic bases are suitable for the preparation of the salts according to the invention, which bases contain as cations alkali metal cations such as, for example, lithium, sodium or potassium, preferably sodium and potassium, but particularly preferably sodium, alkaline earth metal cations such as, for example, magnesium and calcium, ammonium or substituted ammonium ions such as, for example, diethylammonium or triethylammonium. Anions of these bases can be the hydroxyl ion, the bicarbonate ion, the carbonate ion or the anion of an organic acid having 1 to 8, preferably 1–4 C atoms such as, for example, formate, acetate, propionate,α-methylpropionate, 2-ethylhexanoate, but also anions of the general formula RO⁻, in which R represents alkyl having 1–4 C atoms such as, for example, methyl, ethyl, n-propyl, isopropyl, n-butyl, isobutyl-,2-butyl or tert.-butyl, preferably methyl and ethyl. However, additional, possibly very suitable, cations are basic aminoacids such as, for example, lysine or arginine in their protonated forms.

Examples of suitable organic solvents which are miscible with water are ethanol, isopropanol, propanol, butanol, 2-butanol, isobutanol, tert.-butanol, acetone, tetrahydrofuran, 1,4-dioxane or mixtures of these. Ethanol, propanol, isopropanol and acetone are particularly preferred. In order to complete crystallization, a solvent which is not miscible with water such as, for example, diethyl ether, diisopropyl ether and toluene, can also be added to the suspension of the crystals in the mixture of water and the solvent miscible with water.

The concentration of the aqueous solutions of the salt of cefodizim, which is to be brought to crystallization according to the invention by the addition of an organic solvent, is advantageously between about 5 and 50%, preferably between about 10 and 30%.

The total amount of the organic solvent or mixture of solvents to be employed is up to about twenty times the volume of the aqueous solution. The use of an even larger amount is also possible, but, as a rule, has no particular advantages. The mixing of the aqueous solution with the organic solvent or mixture of solvents should be carried out slowly, for example, dropwise, in order to achieve good crystallinity and thus also a high purity of the product.

The crystallization is advantageously carried out at room temperature. However, good results are also obtained at temperatures of, for example, 0° to 60° C. A subsequent stirring time of up to about 3 hours or more completes crystallization.

The crystals of the cefodizim salt thus obtained are separated off by customary laboratory processes such as, for example, filtration, if desired under sterile conditions, and adherent solvent is removed under a slight vacuum. As adducts or solvates, they still contain up to 2 moles of water and up to 2 moles of organic solvent per mole of salt.

The removal of the organic solvent from the crystalline product can be carried out by various means. Thus, it is possible to exchange the organic solvent for water, either in air (with an adequate moisture content, i.e. >50%) or in a closed vessel under a moist atmosphere. The uptake of water is, as a rule, complete after about 12 to 72 hours. The crystals thus treated no longer contain organic solvent and have a water content of 3 to 3.5 moles of water per mole of salt.

If the crystals obtained by filtration are exposed to a high vacuum ( <1 mm Hg), both organic solvent and also water are removed, particularly in the presence of a desiccant, such as, for example, concentrated sulfuric acid or phosphoric anhydride but also potassium hydroxide or sodium hydroxide, and also silica gel (blue gel).

Such a sample again takes up 3 to 3.5 moles of water per mole of salt when it is subjected to the conditions described above for removing organic solvents from the crystalline product, but it does not lose its crystalline properties as defined below. A crystalline salt which contains no water or solvent can also be converted into a solvate by the action of an organic solvent.

Stability investigations carried out with the crystalline sodium salt of cefodizim having various contents of water and solvent show that, in particular, almost completely anhydrous batches showed virtually no decrease in the antibiotic effectiveness on, for example, storing at 60° C. for one month, and thus the advantageous effect of a defined content of water and solvent and a defined crystallinity on the stability of the salt has been proven.

The following examples are intended to illustrate the invention in more detail, but without restricting it to the examples listed.

EXAMPLE 1

Disodium salt of 7-β-[2-(2-aminothiazol-4-yl)-2-synmethoximinoacetamido]-3-(5-carboxymethyl-4-methyl-1,3-thiazol-2-ylthiomethyl)ceph-3-em-4-carboxylic acid (disodium salt of cefodizim).

46.0 g of cefodizim were suspended in 100 ml of water, 13.2 g of anhydrous sodium bicarbonate were added and the mixture was stirred at room temperature until dissolution was complete. The slightly yellow-colored solution was stirred with 2 g of filter carbon, filtered and the filtrate was diluted with water to 150 ml. 1,000 ml of ethanol were added dropwise to this solution at 20°–25° C. with constant stirring. After completion of addition of the ethanol, the mixture was subsequently stirred for 1 hour, cooling in ice, and then the solid was filtered off. 34.1 g of disodium salt of cefodizim were obtained in the form of colorless crystals.

Analysis:
| | | |
|---|---|---|
| Na | calculated | 6.4% |
| (from the sulfated ash) | found | 6.4% |
| $H_2O$ | calculated | 3.7 (1.5 moles) |
| (Karl Fischer method) | found | 3.8 |
| Ethanol | calculated | 9.5 (1.5 moles) |
| (by gas chromatography) | found | 8.5 |
| IR: $\nu_\beta$-lactam | 1,755 cm$^{-1}$ | |
| $^1$H—NMR (d$_6$-DMSO): | δ = 2.14 | (s; C$\underline{H}_2$—thiazole) |
| | 3.23 | (s; C$\underline{H}_2$—COOH and ceph-(-2-C$\underline{H}_2$) |
| | 3.26 | (s; CH$_2$—COOH and ceph-(-2-CH$_2$) |
| | 3.83 | (s; N—O—C$\underline{H}_3$) |
| | 4.03, | (AB system; —C$\underline{H}_2$—S; |
| | 4.51 | J = 13 Hz) |
| | 4.92 | (d; C—6-$\underline{H}$;) J = 5 Hz |
| | 5.03 | (q; C—7-$\underline{H}$;) J = 5 Hz J = 7 Hz |
| Resonance signal of | | |
| Ethanol: 1.04; t; C$\underline{H}_3$ | 6.66 | (s; C—5-thiazole-$\underline{H}$) |
| 3.41; q; C$\underline{H}_2$ | 7.02 | (broad s; $\underline{NH}_2$) |
| | 9.42 | (d; N$\underline{H}$CO; J = 7 Hz) |

X-ray diffraction pattern (Ni-filtered copper radiation; = 1.5418)

| Interplanar spacing d | Relative intensity (J/J$_{max}$) |
|---|---|
| 8.66 | 1.00 |
| 7.63 | 0.43 |
| 7.25 | 0.36 |
| 6.57 | 0.16 |
| 6.32 | 0.49 |
| 5.37 | 0.17 |
| 5.22 | 0.45 |
| 4.96 | 0.35 |
| 4.67 | 0.09 |
| 4.55 | 0.33 |
| 4.33 | 0.46 |
| 4.10 | 0.98 |
| 3.98 | 0.45 |
| 9.90 | 0.40 |
| 3.81 | 0.42 |
| 3.79 | 0.43 |
| 3.73 | 0.40 |
| 3.62 | 0.10 |
| 3.47 | 0.26 |
| 3.39 | 0.43 |
| 3.24 | 0.17 |
| 3.15 | 0.06 |
| 3.08 | 0.18 |
| 2.86 | 0.09 |

Ethanol is removed from such a sample by allowing it to stand in air of sufficient moisture content for 12–16 hours. Thereafter, no alcohol can be detected by NMR spectroscopy, and GC analysis shows a maximum of 1% which can also be removed by extending the procedure.

EXAMPLE 2

Disodium salt of cefodizim 51.0 g of cefodizim and 14.8 g of sodium bicarbonate were dissolved in 220 ml of water. This solution was slowly added dropwise to 4,350 ml of isopropanol at room temperature. After completion of addition, colorless crystals precipitated from the initially turbid white suspension. Stirring was continued for a further 4 hours and the solid was filtered off with suction and dried overnight. After a further 8 hours at 40° C./150 mm Hg over silica gel (blue gel), 54 g of the disodium salt of cefodizim were obtained in the form of colorless crystals. IR:$\nu\beta$-lactam; 1,775 cm$^{-1}$

EXAMPLE 3

Dipotassium salt of cefodizim 5.84 g of cefodizim and 2.0 g of potassium bicarbonate were dissolved in 30 ml of water and the solution was filtered. 300 ml of isopropanol were added to the solution at 20°–25° C. and the mixture was stirred, while cooling in ice, for a further 1 hour. Filtration and drying over KOH produced 3.4 g of the dipotassium salt of cefodizim in the form of colorless crystals.

Analysis:

| | | |
|---|---|---|
| H$_2$O (Karl Fischer method) | calculated found | 1.1% (for 0.5 mole) 1.1% |
| Isopropanol: (by gas chromatography) | calculated found | 4.3% (for 0.5 mole) 5.4% |
| Potassium (from the sulfated ash) | calculated found | 11.1% 10.7% |
| IR: $\nu\beta$-lactam | 1,772 cm$^{-1}$ | |

X-ray diffraction pattern (Ni-filtered copper radiation, $\lambda = 1.5418$ Å)

| Intraplanar spacing d | relative intensity (J/J$_{max}$) |
|---|---|
| 18.01 | 0.98 |
| 12.96 | 0.81 |
| 9.98 | 0.29 |
| 8.51 | 0.30 |
| 8.25 | 0.53 |
| 7.15 | 0.27 |
| 6.63 | 0.19 |
| 6.04 | 0.15 |
| 5.66 | 0.27 |
| 5.41 | 0.52 |
| 5.21 | 0.28 |
| 5.01 | 0.16 |
| 4.80 | 0.18 |
| 4.60 | 0.31 |
| 4.59 | 0.39 |
| 4.52 | 0.43 |
| 4.36 | 0.45 |
| 4.27 | 0.69 |
| 4.11 | 0.86 |
| 4.04 | 1.00 |
| 3.92 | 0.80 |
| 3.72 | 0.61 |
| 3.64 | 0.64 |
| 3.43 | 0.54 |
| 3.13 | 0.44 |
| 2.97 | 0.43 |

The cefodizim employed as starting material can be obtained in the following manner.

6.1 g of 2-(2-mercapto-4-methyl-1,3-thiazol-5-yl)acetic acid were suspended in 75 ml of water and the pH was adjusted to 6.5 with 22 ml of 2N sodium hydroxide solution. The mixture was heated to 70° C. and a solution of 11.9 g of cefotaxim in 75 ml of water was added dropwise at this temperature within 2 hours. The mixture was subsequently stirred for 2 hours (at 70° C.) and the pH was maintained constant at 6.5 by an addition of 2N NaOH solution (amount consumed: about 9 ml of 2N NaOH solution).

Finally, the mixture was cooled down to 25° C., about 38 ml of 2N HCl solution were added (pH decreased to 2.8) and cooled to 0° C. The precipitate was filtered off with suction, thoroughly stirred with 200 ml of water, again filtered off with suction and washed with a further 100 ml of water. After drying under high vacuum over P$_4$O$_{10}$ at about 20° C., 10.5 g of cefodizim were obtained as a light brown colored product.

100 g of the cefodizim thus obtained were finely powdered, suspended in 300 ml of water and brought to solution with sodium bicarbonate. The pH of the solution was adjusted to about 6.5 with dilute hydrochloric acid, the solution, which was slightly cloudy due to suspended material, was filtered and the clear brown colored filtrate was applied to a column which had been prepared as described below:

1 kg of polystryene absorption resin Hp 29 (XAD2 and similar are also suitable) was allowed to swell with methanol and this amount was filled into a 45×10 cm chromatography column and washed with water until free of methanol.

The solution of the crude sodium salt of cefodizim which had been applied was eluted with 6 liters of water. The first fractions, comprising 1.6 liters, contained no product and were discarded. The remaining eluate was acidified to pH 5 with stirring, a few seeding crystals were added and acidification to pH 2.8 was slowly carried out, maintaining the ambient temperature. Stirring was continued for a further 30 minutes and the solid was filtered off. Yield after exhaustive drying over phosphorus pentoxide: 82 g of cefodizim in the form of colorless crystals.

What is claimed is:

1. The crystalline water soluble disodium salt of 7-$\beta$-[2-(2-aminothiazol-4-yl)-2-syn-methoxyiminoacetamido]3-(5-carboxymethyl-4-methyl-1,3-thiazol-2-ylthiomethyl)ceph-3-em-4-carboxylic acid or an adduct or solvate thereof with water and/or an organic solvent.

* * * * *